(12) United States Patent
Park

(10) Patent No.: US 10,039,501 B2
(45) Date of Patent: Aug. 7, 2018

(54) COMPUTER-AIDED DIAGNOSIS (CAD) APPARATUS AND METHOD USING CONSECUTIVE MEDICAL IMAGES

(71) Applicant: Samsung Electronics Co., Ltd., Suwon-si (KR)

(72) Inventor: Jin Man Park, Yongin-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 79 days.

(21) Appl. No.: 14/925,621

(22) Filed: Oct. 28, 2015

(65) Prior Publication Data

US 2016/0117818 A1 Apr. 28, 2016

(30) Foreign Application Priority Data

Oct. 28, 2014 (KR) .................. 10-2014-0147685

(51) Int. Cl.
*A61B 5/00* (2006.01)
*G06T 7/00* (2017.01)
*G06K 9/62* (2006.01)

(52) U.S. Cl.
CPC .......... *A61B 5/7282* (2013.01); *A61B 5/7425* (2013.01); *G06K 9/628* (2013.01); *G06T 7/0012* (2013.01); *G06T 2207/10072* (2013.01); *G06T 2207/20084* (2013.01); *G06T 2207/30096* (2013.01)

(58) Field of Classification Search
CPC combination set(s) only.
See application file for complete search history.

(56) References Cited

U.S. PATENT DOCUMENTS

| 6,075,879 | A | * | 6/2000 | Roehrig | G06F 19/321 |
| | | | | | 382/132 |
| 7,615,008 | B2 | * | 11/2009 | Zhang | A61B 8/0825 |
| | | | | | 382/128 |
| 7,616,836 | B2 | | 11/2009 | Valadez | |
| 7,756,304 | B2 | | 7/2010 | Hossack et al. | |
| 8,014,576 | B2 | | 9/2011 | Collins et al. | |
| 8,213,700 | B2 | * | 7/2012 | Periaswamy | G06K 9/00 |
| | | | | | 382/131 |
| 2005/0100208 | A1 | * | 5/2005 | Suzuki | G06T 5/007 |
| | | | | | 382/157 |
| 2008/0298657 | A1 | * | 12/2008 | Shiraishi | G06T 5/50 |
| | | | | | 382/130 |
| 2009/0318809 | A1 | * | 12/2009 | Okamura | A61B 8/14 |
| | | | | | 600/443 |
| 2012/0275676 | A1 | * | 11/2012 | Haacke | G06T 7/0016 |
| | | | | | 382/131 |
| 2014/0376792 | A1 | * | 12/2014 | Matsuzaki | A61B 1/00009 |
| | | | | | 382/128 |

* cited by examiner

*Primary Examiner* — Tsung-Yin Tsai
(74) *Attorney, Agent, or Firm* — Jefferson IP Law, LLP

(57) ABSTRACT

A Computer-Aided Diagnosis (CAD) apparatus may include: an image receiver configured to receive consecutive medical images; an image analyzer configured to divide the received consecutive medical images into sequence groups by a predetermined number, separate images in a sequence group, among the sequence groups, into a first image group and a second image group, and perform parallel analysis on the first image group and the second image group; and a display configured to output on a screen a result of the analyzing of the first image group and the second image group.

14 Claims, 7 Drawing Sheets

COMPUTER-AIDED DIAGNOSIS (CAD) APPARATUS AND METHOD USING CONSECUTIVE MEDICAL IMAGES

CROSS-REFERENCE TO RELATED APPLICATION(S)

This application claims the benefit under 35 USC 119(a) of Korean Patent Application No. 10-2014-0147685 filed on Oct. 28, 2014, in the Korean Intellectual Property Office, the entire disclosure of which is incorporated herein by reference for all purposes.

BACKGROUND

1. Field

The following description relates to a Computer-Aided Diagnosis (CAD) apparatus and method for high-speed diagnosis using consecutive medical images.

2. Description of Related Art

In general, doctors identify an image to be used to diagnose a disease by receiving and analyzing ultrasonic medical images in real time from a probe, which is put in contact with a diseased area of a patient's body. Alternatively, doctors analyze a two- or three-dimensional (2D/3D) image sequence that is stored offline. In particular, when using a medical image acquired in real time from a probe or using a 3D volume image that is stored offline, the doctors determine whether the diseased area of a patient's body is benign or malignant based on the set of received consecutive 2D images that are displayed on a screen.

Recently, medical images are analyzed using a Computer-Aided Diagnosis (CAD) system. Such an approach potentially automates analysis of medical images to make a diagnosis. The CAD system detects and tracks a lesion using medical images, and classifies whether a lesion is benign or malignant. Generally, medical images are captured at 30 or more frames per second in the case of real-time image diagnosis. However, with limited computing performance of a CAD system, it is hard to perform analysis and classification on a medical image in real time, because of the large amounts of data involved and the complicated calculations required to properly process the images.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, a Computer-Aided Diagnosis (CAD) apparatus includes: an image receiver configured to receive consecutive medical images; an image analyzer configured to divide the received consecutive medical images into sequence groups by a predetermined number, separate images in a sequence group, among the sequence groups, into a first image group and a second image group, and analyze the first image group and the second image group in parallel; and a display configured to output a result of the analyzing of the first image group and the second image group.

The image analyzer may be further configured to separate the images in the sequence group by classifying a reference image including a first frame in the sequence group as the first image group and classifying other frames in the sequence group as the second image group.

The image analyzer may include a first image analyzer configured to analyze the first image group using a first analytical algorithm; and a second image analyzer configured to analyze the second image group using a second analytical algorithm that is different from the first analytical algorithm.

The second analytical algorithm may require less analysis time in comparison to the first analytical algorithm.

The first image analyzer may be further configured to analyze an entire area of an image in the first image group on a pixel-by-pixel basis or on a predetermined pixel group-by-pixel group basis using the first analytical algorithm.

The second image analyzer may be further configured to analyze all frames of the second image group in sequence using the second analytical algorithm by measuring a variation in each block, among blocks of the frames of the second image group, between a specific frame and a previous frame thereof in the second image group, and analyzing the specific frame based on the measured variation.

The second image analyzer may be further configured to calculate a lesion presence probability for each block in all the frames of the second image group based on the measured variation, and detect a lesion area in each of the frames of the second image group based on the calculated lesion presence probability.

The image analyzer may be further configured to generate an integrated result of analysis of the second image group by combining results of analysis of all frames of the second image group, and generate an integrated result of analysis of the sequence group by combining a result of analysis of the first image group and the integrated result of analysis of the second image group.

The integrated analyzer may be further configured to assign a preset weighted value to a lesion presence probability for each block in each of all the frames of the second image group, add weighted lesion presence probabilities for a corresponding block in all the frames of the second image group, and generate the integrated result of analysis of the second image group based on a sum of the weighted lesion presence probabilities.

The image analyzer may further include a re-analyzer configured to re-determine a lesion area in each frame of the second image group by performing backtracking in reverse of an order of receiving all frames of the sequence group based on the integrated result of analysis of the sequence group and the integrated result of analysis of the second image group.

The CAD apparatus may further include an image preprocessing component configured to perform preprocessing on the received consecutive medical images, the preprocessing including one or more of normalization, channel separation, and scaling.

In another general aspect, a Computer-Aided Diagnosis (CAD) method includes: receiving, at a receiver, consecutive medical images; dividing, at an image analyzer, the received consecutive images into sequence groups by a predetermined number; separating images in a sequence group, among the sequence groups, into a first image group and a second image group; analyzing the first image group and the second image group in parallel; and outputting, on a screen, a result of the analyzing of the first image group and the second image group.

The separating of images in the sequence group may include classifying a reference image comprising a first frame in the sequence group as the first image group and classifying other frames in the sequence group as the second image group.

The analyzing of the first image group and the second image group may include: analyzing the first image group using a first analytical algorithm; and analyzing the second image group using a second analytical algorithm that is different from the first analytical algorithm.

The second analytical algorithm may require relatively less analysis time in comparison to the first analytical algorithm.

The analyzing of the first image group may include analyzing an entire area of an image in the first image group on a pixel-by-pixel basis or on a predetermined pixel group-by-pixel group basis using the first analytical algorithm The analyzing of the second image group may include analyzing all frames of the second image group in sequence using the second analytic algorithm by measuring a variation in each block, among blocks of the frames of the second image group, between a specific frame and a previous frame thereof in the second image group, and analyzing the specific frame based on the measured variation.

The analyzing of the second image group may include calculating a lesion presence probability for each block in all the frames of the second image group based on the measured variation, and detecting a lesion area from each of the frames of the second image group based on the calculated lesion presence probability.

The analyzing of the first image group and the second image group may include: generating an integrated result of analysis of the second image group by combining results of analysis of all frames of the second image group; and generating an integrated result of analysis of the sequence group by combining a result of analysis of the first image group and the integrated result of analysis of the second image group.

The generating of the integrated result of analysis of the second image group may include assigning a preset weighted value to a lesion presence probability for each block in each of all the frames of the second image group, adding weighted lesion presence probabilities for a corresponding block in all the frames of the second image group, and generating the integrated result of analysis of the second image group based on a sum of the weighted lesion presence probabilities.

The analyzing of the first image group and the second image group may further include re-determining a lesion area in each frame of the second image group by performing backtracking in reverse of an order of receiving all frames of the sequence group based on the integrated result of analysis of the sequence group and the integrated result of analysis of the second image group.

The CAD method may further include performing pre-processing on the received consecutive medical images, the preprocessing including one or more of normalization, channel separation, and scaling.

According to yet another general aspect, a Computer-Aided Diagnosis (CAD) method may include: separating, at a processor, a sequence of image frames into a first image group and a second image group; analyzing, at the processor, the first image group and the second image group by applying different analytical algorithms to the first image group and the second image group; and outputting, from the processor, a result of the analyzing of the first image group and the second image group.

The analyzing of the first image group and the second image group may include analyzing the first image group and the second image group in parallel.

The first analytical algorithm and the second analytical algorithm may differ in speed and accuracy.

Other features and aspects may be apparent from the following detailed description, the drawings, and the claims.

BRIEF DESCRIPTION OF THE DRAWINGS

Throughout the drawings and the detailed description, the same reference numerals refer to the same elements. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the methods, apparatuses, and/or systems described herein will be apparent to one of ordinary skill in the art. The sequences of operations described herein are merely examples, and are not limited to those set forth herein, but may be changed as will be apparent to one of ordinary skill in the art, with the exception of operations necessarily occurring in a certain order. Also, descriptions of functions and constructions that are well known to one of ordinary skill in the art may be omitted for increased clarity and conciseness.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

Throughout the Specification, the term "image group" has been used. Here, an image group refers to one or more frames that are gathered by appropriate medical imaging that are treated as a unified set of images for analysis. For example, one image group is an image group including a single frame that is a reference frame that is analyzed by itself. Alternatively, in another example, an image group includes several frames, such as a succession of consecutive frames that are grouped and analyzed together.

Hereinafter, a Computer-Aided Diagnosis (CAD) apparatus and method using consecutive medical images are described further with reference to the drawings.

Figure 1:
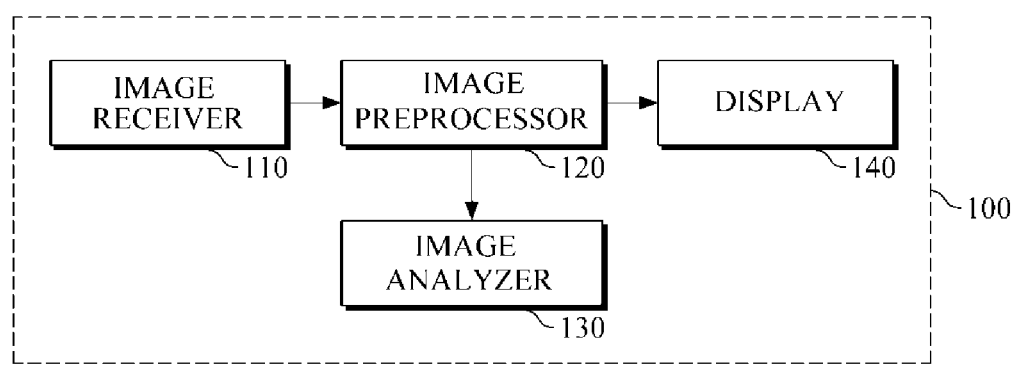
FIG. 1 is a block diagram illustrating a Computer-Aided Diagnosis (CAD) apparatus according to an example.

FIG. 1 is a block diagram illustrating a CAD apparatus according to an example.

Referring to the example of FIG. 1, a CAD apparatus 100 includes an image receiver 110, an image preprocessor 120, an image analyzer 130, and a display 140.

The image receiver 110 receives medical images and outputs consecutive two-dimensional (2D) images. For example, a medical image is an ultrasonic image of a diseased area of a patient's body, which is captured by a probe. However, aspects of the present examples are not limited thereto, and in other examples the medical image is a Computed Radiography (CR) image, a Computed Tomography (CT) image, a Magnetic Resonance Image (MRI), or another appropriate medical image.

The image receiver 110 receives an image in units of frames in real time. Alternatively, the image receiver 110 receives a medical image that is stored in various forms, such as a two- or three-dimensional (2D/3D) image or a video, and processes the received medical image to output consecutive 2D images that form an image sequence.

The image preprocessor 120 preprocesses images output from the image receiver 110 using various preprocessing algorithms in order to smoothly extract abstract image information which is necessary for diagnosis. In examples, the preprocessing algorithms include spatial normalization, channel separation, scaling, timing correction, image realignment, spatial smoothing, and other appropriate preprocessing algorithms. In general, these preprocessing algorithms are algorithms that are designed to remove irrelevant discrepancies form the images so that the most relevant information about the image is easily apparent later in the image analysis process.

In the example where the preprocessor 120 preprocesses consecutive images output from the image receiver 110, the image analyzer 130 further divides preprocessed consecutive images into sequence groups by a predetermined number. For example, the predetermined number is appropriately set in consideration of computing performance of the CAD apparatus 100 and performance of an image acquiring apparatus that acquires images of a diseased area of a patient's body in real time.

Once a sequence group is formed, the image analyzer 130 separates images in the sequence group into a first image group and a second image group in order to analyze all the images in the sequence group in parallel. However, the disclosure is not limited to separating images of a sequence group into first and second image groups, and images of a sequence group may be separated into three or more subgroups in consideration of computing performance and architecture of each CAD apparatus 100 and the number of the CAD apparatuses 100 that performs diagnosis. For example, if multiple cores or processors are available for processing the images, it is appropriate to divide the images into more groups for parallel processing.

In addition, the image analyzer 130 separates images in a sequence group by classifying reference images including the first frame in the sequence group as the first image group, and the other images in the sequence group as the second image group. At this point, by considering performance of the CAD apparatus 100 and a processing rate of each analytical algorithm to be applied to the first and second image groups, in an example, two or more frames are predetermined to be reference images. For example, by considering a processing rate of an analytical algorithm for the first image group and a processing rate of an analytical algorithm for the second image group, two or more consecutive frames including the first frame are classified to be reference images so that the respective analytical algorithms are able to complete the analysis almost simultaneously and speed up processing by processing in parallel.

The image analyzer 130 analyzes sequence groups in parallel by applying the respective analytical algorithms to the first and second image groups. In an example, the respective analytical algorithms to be applied to the first and second image groups are heterogeneous analytical algorithms that differ in speed and accuracy of analysis. For example, the analysis includes detecting and tracking a lesion area, such as to establish its boundaries and location, and classifying whether a detected lesion is malignant or benign.

Thus, the display 140 outputs consecutive images output by the image receiver 110 or an image preprocessed by the image preprocessor 120 on a screen. In addition, after the image analyzer 130 completes analyzing a sequence group, the display 140 outputs a result of analysis of the sequence group on the screen. By producing this output, the CAD apparatus 10 is able to communicate the results of the CAD processing to a human user for further usage.

For example, the display 140 displays the result of analysis to overlay a corresponding image, or outputs the result of analysis in a specific area of the screen, except for an area where a corresponding image is displayed. For example, in order to help a user to easily identify a lesion area, the display 140 outputs a distinguishing mark, such as a circle, a square, and/or a cross, at a corresponding location on the output image using lesion area information, for example, location and size of a lesion area, included in the result of analysis.

Figure 2:
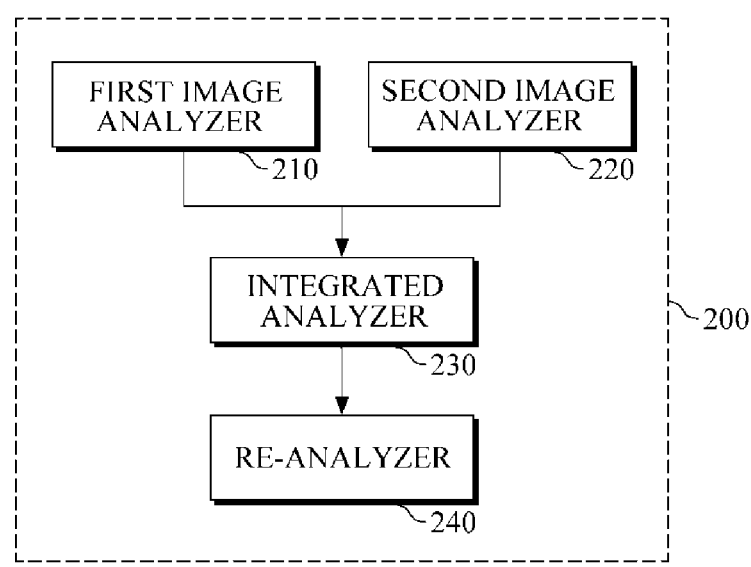
FIG. 2 is a block diagram illustrating an image analyzer shown in FIG. 1.

FIG. 2 is a block diagram illustrating an example image analyzer 200 corresponding to the image analyzer 130 shown in FIG. 1.

Referring to FIG. 2, the image analyzer 200 includes a first image analyzer 210, a second image analyzer 220, an integrated analyzer 230, and a re-analyzer 240.

The first image analyzer 210 analyzes the first image group among images of a sequence group using the first analytical algorithm, and outputs the result of analysis. For example, the first analytical algorithm is an algorithm which performs accurate analysis of frames but requires relatively long time for the analysis, for example, a Convolution Neural Network (CNN) analysis algorithm.

For example, the first image analyzer 210 extracts abstract medical image information from the first image group, and then detects, tracks, and determines a lesion area based on the extracted medical image information. The abstract medical image information is clinically meaningful image features, for example, visual pattern information of a tissue. Such information is helpful for classifying whether a lesion is malignant or benign. Thus, medical image features are classified into predetermined categories.

For example, the medical image information includes feature information, such as shape, echo pattern, orientation, boundary, texture and intensity of a lesion. Thus, in the case of a breast ultrasonic image, the medical image information includes a lesion's characteristics that are analyzed in accordance with classification of Breast Imaging Reporting And Data System (BI-RADS) lexicons. Similarly, in the case of a liver ultrasonic image, the medical image information includes a lesion's characteristics in accordance with classification of Liver Imaging Reporting and Data System (LI-RADS) lexicons.

By analyzing the entire area of the first image group on a pixel-by-pixel basis or on a predetermined pixel group-by-pixel group basis, the first image analyzer 210 extracts medical image features and outputs a result of analysis.

The second image analyzer 220 analyzes the second image group among images of a sequence group. In this case, the second image analyzer 220 extracts abstract medical image information from each frame of the second image group using the second analytical algorithm, and then performs analysis on each frame, such as by detecting and classifying a lesion area. For example the second analytical algorithm is a heterogeneous analytical algorithm that requires less analysis time, compared to the first analytical algorithm.

For example, the second image analyzer 220 divides each frame of the second image group into a grid of blocks in sequence, and measures a change in the images, including a variation in a block belonging to both of a previous frame and the current frame. At this point, in an example, a variation in the first frame of the second image group is measured by a comparison with the first image group on a block unit basis.

In addition, based on the measured variations, the second image analyzer 220 calculates a probability of lesion to exist in each block, hereinafter, referred to as a lesion presence probability for each block. In this case, lesion presence probability information according to image variation is preset, and a lesion presence probability that corresponds to variation in each block is calculated using the lesion presence probability information. In addition, in an example, if there is an area including a block with the calculated lesion presence probability greater than a preset threshold, the second image analyzer 220 determines the area to be a lesion area.

Among various analytical algorithms, the first analytical algorithm and the second analytical algorithm are predetermined by various standards, such as the number of the CAD apparatuses 100 which perform analysis, computing performance of each CAD apparatus 100, a predetermined number of images in a sequence group, analysis speed, and analysis accuracy. Thus, overall, available computing resources are used to decide which analytical algorithms are the best choice for analyzing the images. In various examples, an analytical algorithm may include AdaBoost, Deformable Part Models (DPM), Support Vector Machine (SVM), Decision Tree, Deep Belief Network (DBN), and/or Convolutional Neural Network (CNN). However, these are merely examples, and in other examples appropriate alternative algorithms may be used.

In addition, the first image analyzer 210 and the second image analyzer 220 perform analysis in parallel using the first analytical algorithm and the second analytical algorithm simultaneously. The first image analyzer 210 and the second image analyzer 220 are included in a single CAD apparatus 100 to perform parallel analysis using threads, or are included in two different CAD apparatuses 100 to perform parallel analysis.

The integrated analyzer 230 generates an integrated result of analysis of a sequence group by combining a result of analysis of the first image group and a result of analysis of the second image group. In this case, the integrated analyzer 230 sequentially classifies a lesion area of each frame of the second image group based on the result of analysis of the first image group, and generates an integrated result of analysis of the second image group by combining all classification results regarding the second image group. In addition, the integrated analyzer 230 generates an integrated result of analysis of a sequence group by incorporating the result of analysis of the first image group to the integrated result of analysis of the second image group.

For example, the integrated analyzer 230 assigns a preset weighted value to a lesion presence probability for each block of a frame of the second image group, and generates an integrated result of analysis of the second image group based on the weighted lesion presence probabilities. Specifically, the integrated analyzer 230 generates an integrated result of analysis of the second image group by adding up weighted lesion presence probabilities for a corresponding block in all the frames of the second image group, and then determining and classifying a lesion area of the second image group based on a sum of the weighted lesion presence probabilities.

In the example of FIG. 2, the re-analyzer 240 determines a lesion area in each frame of a sequence group based on the integrated result of analysis of the sequence group, the integrated result of analysis of the second image group, and the result of analysis of each frame of the second image group. In this case, the re-analyzer 240 determines a final lesion area in each frame of a sequence group by performing backtracking in reverse of an order of receiving all frames in the sequence group based on the integrated result of analysis of the sequence group and variation in a block in each frame of the second image group. Specifically, the backtracking process is performed in an order from the last input frame of the second image group to the first input frame of the first image group.

Figure 3:
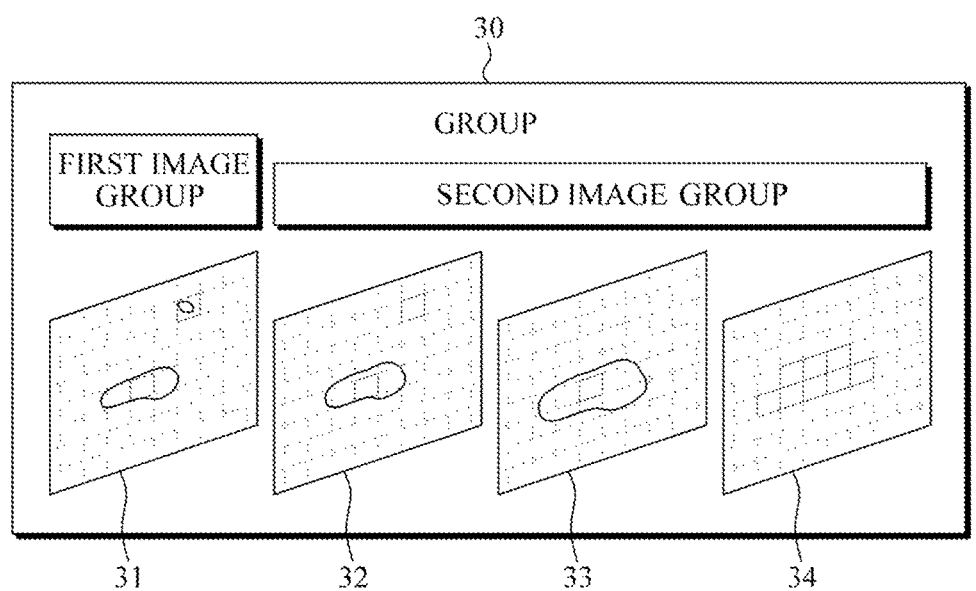
FIGS. 3, 4, and 5 are diagrams illustrating an example of analyzing consecutive images.
Figure 4:
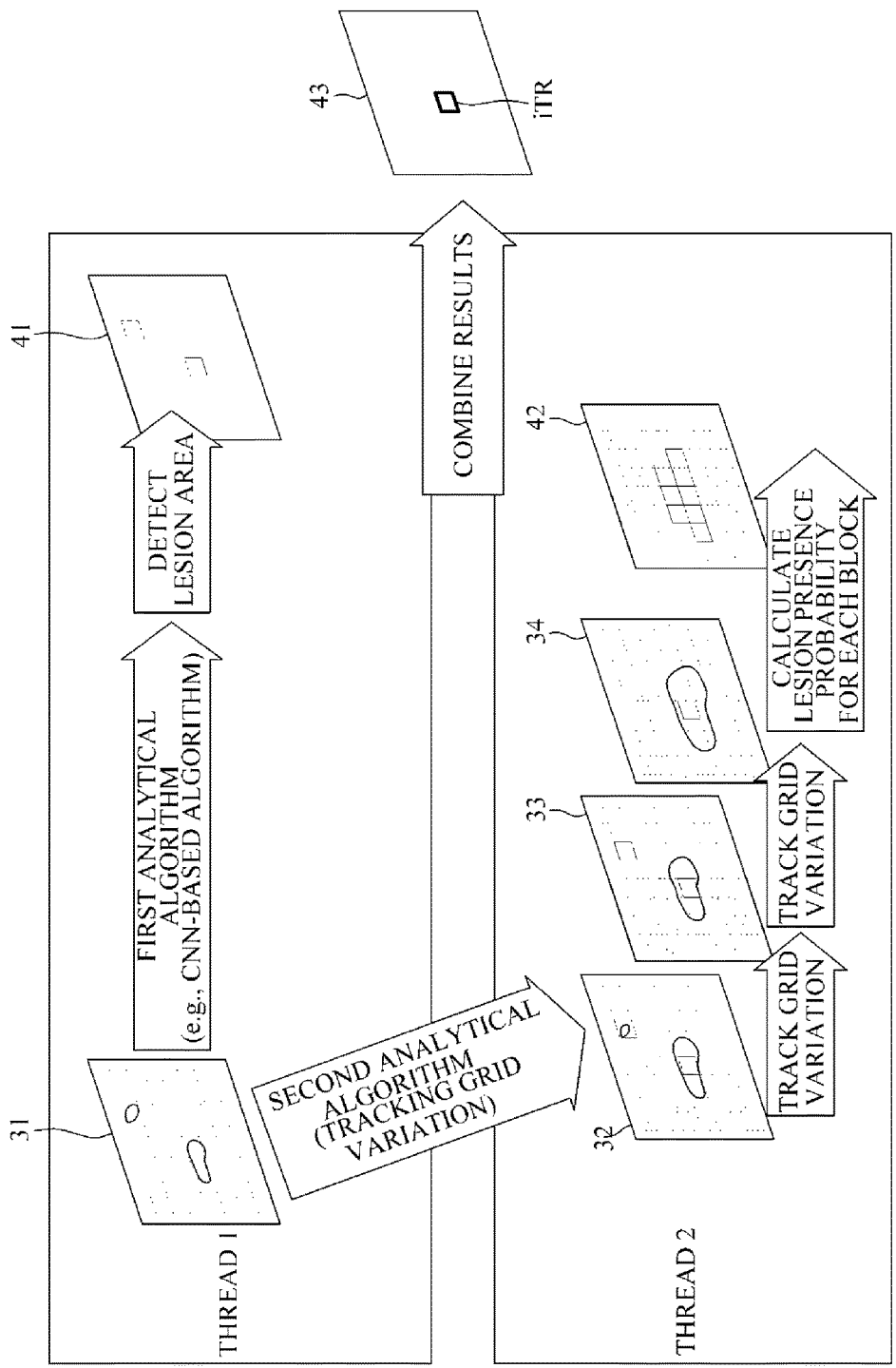
Figure 5:
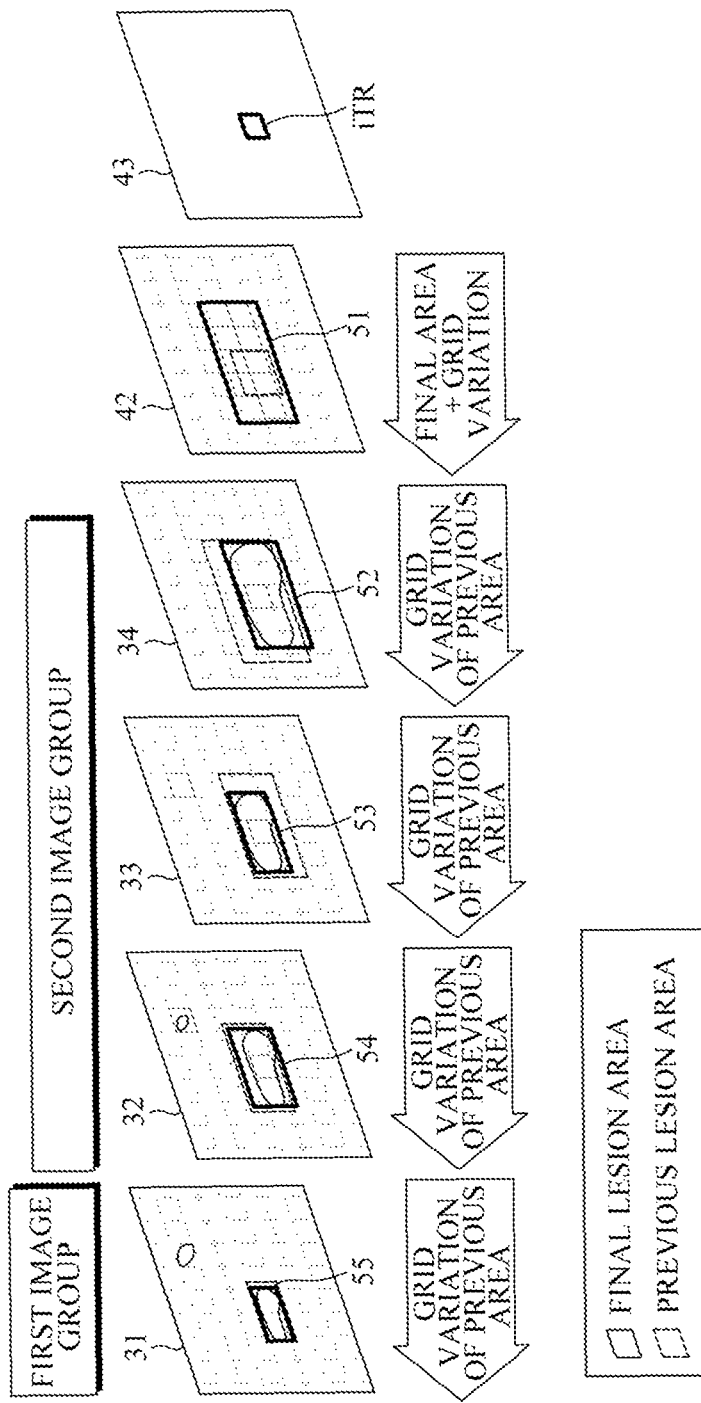

FIGS. 3, 4, and 5 are examples of ways in which consecutive images are diagnosed.

Referring to FIGS. 3, 4, and 5, an example operation of the aforementioned CAD apparatus 100 is described further.

Referring to FIG. 3, the image receiver 110 processes a received medical image and outputs consecutive 2D frames. Four frames 31, 32, 33, and 34 are illustrated in FIG. 3 for explanation as examples, but aspects of operation of the CAD apparatus 100 are not limited to this particular example.

In the case where four frames are predetermined to be a unit of sequence group, the image analyzer 120 groups the four consecutive frames 31, 32, 33, and 34 into a sequence group 30, as illustrated in FIG. 3. That is, the image analyzer 130 waits until the first frame 31 to the fourth frame 34 are output from the image receiver 110, and, once the fourth frame 34 is output, the image analyzer 130 groups the four frames 31, 32, 33, and 34 into the sequence group 30.

Once the sequence group 30 is formed, the image analyzer 130 proceeds with appropriate analysis of each of the frames 31, 32, 33, and 34 in the sequence group 30. As illustrated in FIG. 3, the image analyzer 130 may separate the frames 31, 32, 33, and 34 in the sequence group 30 by classifying the first frame 31, which is predetermined to be a reference frame, as the first image group, and classifying the other frames 32, 33, and 34 as the second image group. Then, the image analyzer 130 analyzes the first image group and the second image group in parallel simultaneously.

Specifically, referring to FIG. 4, the image analyzer 130 processes a thread 1 of the first image group, including the frame 31, and a thread 2 of the second image group, including the frames 32, 33, and 34, in parallel. As illustrated in FIG. 4, the image analyzer 130 applies the first analytical algorithm to the first image group to detect a lesion area and output a result of analysis 41. In addition, the image analyzer 130 applies the second analytical algorithm to the second image group to analyze the frames 32, 33, and 34 sequentially. Specifically, the image analyzer 130 performs analysis by estimating variations in each block between the first frame 32 and the previous frame 31, performs analysis by estimating variation in each block between the second frame 33 and the first frame 32, and performs analysis by estimating variation in each block between the third frame 34 and the second frame 33.

Once all the frames 32, 33, and 34 of the second image group are completely analyzed, the image analyzer 130 combines the results of analysis of the frames 32, 33, and 34, and outputs an integrated result of analysis 42 of the second image group. Then, the image analyzer 130 outputs an integrated result of analysis 43 including a final lesion area (iTR) of the sequence group 30, by combining the result of analysis 41 of the first image group and the integrated result of analysis 42 of the second image group.

Referring to FIG. 5, the image analyzer 130 determines and classifies a final lesion area of all the frames 31, 32, 33, and 34 of the sequence group 30 based on the integrated result of analysis 43 of the sequence group 30. As described below, a final lesion area of all the frames 31, 32, 33, and 34 is determined and classified by performing backtracking in reverse of an order of receiving the frames 31, 32, 33, and 34.

As illustrated in FIG. 5, the image analyzer 130 determines a lesion area 51 as the integrated result of analysis 42 of the second image group using the integrated result of analysis 43 of the sequence group 30, which is, for example, information on the final lesion area (iTR). In this case, a previous lesion area that is taken into consideration to determine a final lesion area 51 regarding the integrated result of analysis 42 of the second image is displayed with a dotted-line.

Similarly, once the final lesion area 51 regarding the integrated result of analysis 42 of the second image is determined, the image analyzer 130 determines a final lesion area 52 in the last frame 34 using the final lesion area 51 and a variation in each block of the last frame 34.

Through this process, the image analyzer 130 determines final lesion areas 53, 54, and 55 in the other corresponding frames 33, 32, and 31, respectively. The previous lesion areas that have been taken into consideration to determine the final lesion areas 51, 52, 53, and 54 in the frames 34, 33, 32, and 31 are displayed in the respective frames 34, 33, 32, and 31 with a dotted-line.

Figure 6:
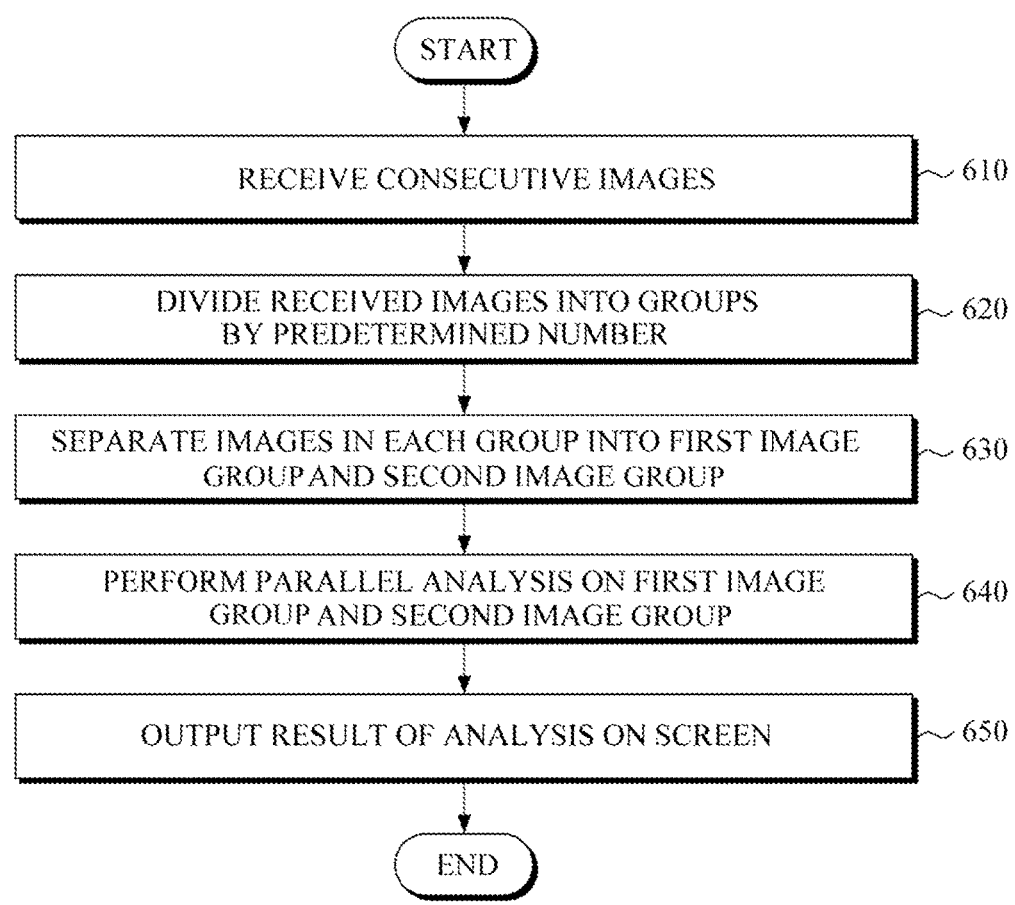
FIG. 6 is a flowchart illustrating a CAD method according to an example.
Figure 7:
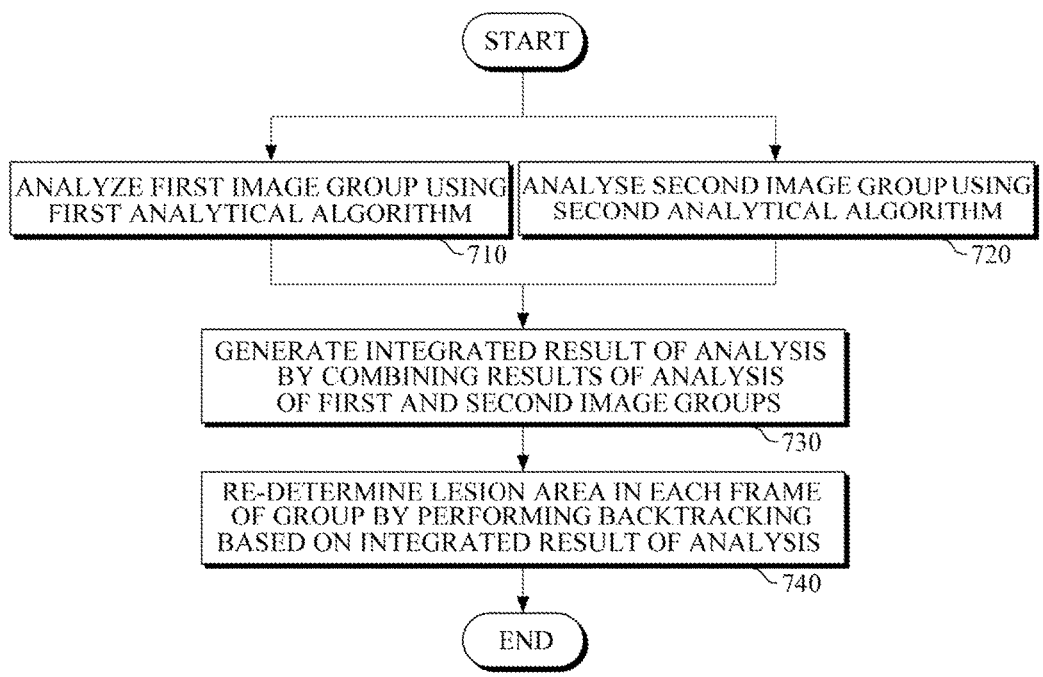
FIG. 7 is a flowchart illustrating an image analyzing operation shown in FIG. 6.

FIG. 6 is a flowchart illustrating a CAD method performed by the CAD apparatus of FIG. 1 according to an example. FIG. 7 is a flowchart illustrating an image analyzing operation shown in the example of FIG. 6.

Referring to FIG. 6, in operation 610, the CAD apparatus 100 receives medical images that are organized as consecutive images. For example, a medical image to be received may be an ultrasonic image of a diseased area of a patient's body, which is captured by a probe, a CR image, a CT image, an MRI, and any one of various appropriate medical images. The output images may be pre-processed using various preprocessing algorithms, as discussed further above, in order to smoothly extract abstract image information that is essential for diagnosis and analysis of the images.

Then, in operation 620, the CAD apparatus 100 groups the output consecutive images into groups so that each group forms a sequence group. The number of images in a sequence group may be set appropriately in consideration of performance of an image acquiring device, the number of the CAD apparatuses 100 and computing performance of each CAD apparatus 100. Thus, the number of images may be set in consideration of the amount and type of computing resources available to process the images.

Then, in operation 630, the CAD apparatus 100 separates images of a sequence group into the first image group and the second image group. For example, the first image group is a reference frame, that is, the first input frame, in the images in the sequence group, and the second image group includes the other frames. However, other groupings of frames in a sequence group are possible, and may be used in other examples in an appropriate manner.

Then, in operation 640, the CAD apparatus 100 analyzes the first image group and the second image group in parallel by applying different analytical algorithms to the first image group and the second image group. The analytical algorithms to be applied to the first image group and the second image group, respectively, are heterogeneous analytical algorithms that are different in speed and accuracy of analysis. The algorithms are chosen appropriately based on factors such as the number of frames in the groups and other factors that dictate how to process the frames most effectively.

Referring to FIG. 7, operation 640 of analyzing the first image group and the second image group is described further.

First, the CAD apparatus 100 analyzes the first frame in the sequence group using the first analytical algorithm in 710, and, at the same time, analyzes all frames in the second image group in parallel using the second analytical algorithm in 720.

At this point, the first and second analytical algorithms may be heterogeneous analytical algorithms that are predetermined by various standards among various analytical algorithms. Such standards include, for example, an analytical purpose, the number of analytic apparatuses, computing performance of each analytic apparatus, the number of images of a sequence group, speed of analysis, and accuracy of analysis.

For example, the first analytical algorithm may be an algorithm that requires relatively long time for analysis with greater analysis accuracy, compared to the second analytical algorithm which requires relatively less time for analysis with lesser analysis accuracy. The analytical algorithms may include, for example, AdaBoost, DPM, SVM, Decision Tree, DBN, CNN, and the like.

In operations 710 and 720, the CAD apparatus 100 extracts abstract medical image information from each of the first and second image groups, respectively, and then detects, tracks, and classifies a lesion area using the extracted medical image information. The abstract medical image information includes, for example, a lesion's characteristics, such as shape, echo pattern, orientation, boundary, texture, intensity, and the like. In the case of a breast ultrasonic image, the abstract medical image information may be a lesion's characteristics in accordance with BI-RADS lexicon classification. In the case of a liver ultrasonic image, the abstract medical image information may be a lesion's characteristics in accordance with LI-RADS lexicon classification.

In addition, in operation 710, the CAD apparatus 100 analyzes the entire area of the first frame on a pixel-by-pixel basis or on a pixel-group-unit basis.

In addition, in operation 720, the CAD apparatus 100 divides each frame of the second image group into blocks, measures variation in each block between a previous frame and the current frame, and analyzes the second image group based on the measured variation in each block. Once the variation in each block of each frame of the second image group is measured, the CAD apparatus 100 calculates a lesion presence probability in each block based on the variation in each block, and detects a lesion area in each frame of the second image group based on the calculated lesion presence probability.

Then, in operation 730, after results of analysis of the first and second image groups are output, the CAD apparatus 100 generates an integrated result of analysis of a sequence group by combining the results of analysis of the first and second image groups. Specifically, the CAD apparatus 100 assigns a predetermined weighted value to the calculated lesion presence probability for each block of all frames of the second image group. The CAD apparatus 100 generates the integrated result of analysis of the second image group by adding weighted lesion presence probabilities for a corresponding block in all the frames of the second image group, and then determining and classifying a lesion area of the second image group based on a sum of the weighted lesion presence probabilities. Then, the CAD apparatus 100 generates the integrated result of analysis of the sequence group by combining a result of analysis of the first image group and the integrated result of analysis of the second image group.

In operation 740, based on the integrated result of analysis of the sequence group generated in operation 730, the CAD apparatus 100 re-determines a lesion area in each frame of the sequence group and classifies whether the lesion area is a benignancy/malignancy. At this point, by performing backtracking in reverse of an order of all frames in the sequence group based on the integrated result of analysis of the sequence group and the integrated result of analysis of the second image group, the CAD apparatus 100 analyzes all the frames, for example, by re-determining and classifying a lesion area.

Referring again to FIG. 6, once the sequence group is completely analyzed, the CAD apparatus 100 displays the result of analysis on a screen in operation 650. For example, the result of analysis may be displayed to overlay a corresponding image, or may be displayed in a specific area on the screen, except the area where the corresponding image is displayed. In order to help a user to easily identify a lesion area, a distinguishing mark, such as a circle, a square, or a cross, may be displayed to overlay the image on the screen by using lesion area information included in the result of analysis.

The apparatuses, units, modules, devices, and other components illustrated in FIGS. 1 and 2 (e.g., the image receiver 110, the imager preprocessor 120, the image analyzer 130/200, the display 140, the first and second image analyzers 210 and 230, the integrated analyzer 230 and the re-analyzer 240) that perform the operations described herein with respect to FIGS. 3-7 are implemented by hardware components. Examples of hardware components include controllers, sensors, generators, drivers, and any other electronic components known to one of ordinary skill in the art. In one example, the hardware components are implemented by one or more processors or computers. A processor or computer is implemented by one or more processing elements, such as an array of logic gates, a controller and an arithmetic logic unit, a digital signal processor, a microcomputer, a programmable logic controller, a field-programmable gate array, a programmable logic array, a microprocessor, or any other device or combination of devices known to one of ordinary skill in the art that is capable of responding to and executing instructions in a defined manner to achieve a desired result. In one example, a processor or computer includes, or is connected to, one or more memories storing instructions or software that are executed by the processor or computer. Hardware components implemented by a processor or computer execute instructions or software, such as an operating system (OS) and one or more software applications that run on the OS, to perform the operations described herein with respect to FIGS. 3-7. The hardware components also access, manipulate, process, create, and store data in response to execution of the instructions or software. For simplicity, the singular term "processor" or "computer" may be used in the description of the examples described herein, but in other examples multiple processors or computers are used, or a processor or computer includes multiple processing elements, or multiple types of processing elements, or both. In one example, a hardware component includes multiple processors, and in another example, a hardware component includes a processor and a controller. A hardware component has any one or more of different processing configurations, examples of which include a single processor, independent processors, parallel processors, single-instruction single-data (SISD) multiprocessing, single-instruction multiple-data (SIMD) multiprocessing, multiple-instruction single-data (MISD) multiprocessing, and multiple-instruction multiple-data (MIMD) multiprocessing.

The methods illustrated in FIGS. 3-7 that perform the operations described herein with respect to FIGS. 1 and 2 are performed by a processor or a computer as described above executing instructions or software to perform the operations described herein.

Instructions or software to control a processor or computer to implement the hardware components and perform the methods as described above are written as computer programs, code segments, instructions or any combination thereof, for individually or collectively instructing or configuring the processor or computer to operate as a machine or special-purpose computer to perform the operations performed by the hardware components and the methods as described above. In one example, the instructions or software include machine code that is directly executed by the processor or computer, such as machine code produced by a compiler. In another example, the instructions or software include higher-level code that is executed by the processor or computer using an interpreter. Programmers of ordinary skill in the art can readily write the instructions or software based on the block diagrams and the flow charts illustrated in the drawings and the corresponding descriptions in the specification, which disclose algorithms for performing the operations performed by the hardware components and the methods as described above.

The instructions or software to control a processor or computer to implement the hardware components and perform the methods as described above, and any associated data, data files, and data structures, are recorded, stored, or fixed in or on one or more non-transitory computer-readable storage media. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, and any device known to one of ordinary skill in the art that is capable of storing the instructions or software and any associated data, data files, and data structures in a non-transitory manner and providing the instructions or software and any associated data, data files, and data structures to a processor or computer so that the processor or computer can execute the instructions. In one example, the instructions or software and any associated data, data files, and data structures are distributed over network-coupled computer systems so that the instructions and software and any associated data, data files, and data structures are stored, accessed, and executed in a distributed fashion by the processor or computer.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A computer-aided diagnosis (CAD) apparatus comprising:
   a display;
   a memory configured to store instructions therein; and
   at least one processor, upon execution of the instructions, configured to:
      receive consecutive medical images,
      generate at least one sequence group by grouping the received consecutive medical images by a predetermined number of consecutive images,
      separate images included in each sequence group into a first image group and a second image group, wherein the first image group comprises at least one reference image comprising a first frame in the each sequence group, and the second image group comprises other frames included in the each sequence group,
      analyze the first image group using a first analytical algorithm and the second image group using a second analytical algorithm that is different from the first analytical algorithm in parallel, and
      output a result of the analyzing of the first image group and the second image group on the display,
      wherein the at least one processor is further configured to separate the first image group and the second image group based on at least one a performance of the CAD, a processing rate of the first analytical algorithm, and a processing rate of the second analytical algorithm,
      wherein the at least one processor is further configured to analyze all frames of the second image group in sequence using the second analytical algorithm by measuring a variation in each block, among blocks of the frames of the second image group, between a specific frame and a previous frame thereof in the second image group and analyzing the specific frame based on the measured variation, and
      wherein the at least one processor is further configured to calculate a lesion presence probability for each block in all the frames of the second image group based on the measured variation, and detect a lesion area in each of the frames of the second image group based on the calculated lesion presence probability.

2. The CAD apparatus of claim 1, wherein the second analytical algorithm requires less analysis time in comparison to the first analytical algorithm.

3. The CAD apparatus of claim 1, wherein the at least one processor is further configured to analyze an entire area of the at least one reference image on a pixel-by-pixel basis or on a predetermined pixel group-by-pixel group basis using the first analytical algorithm.

4. The CAD apparatus of claim 1, wherein the at least one processor is further configured to:
   generate an integrated result of analysis of the second image group by combining results of analysis of all frames of the second image group, and
   generate an integrated result of analysis of the sequence group by combining a result of analysis of the first image group and the integrated result of analysis of the second image group.

5. The CAD apparatus of claim 4, wherein the at least one processor is further configured to assign a preset weighted value to a lesion presence probability for each block in each of all the frames of the second image group, add weighted lesion presence probabilities for a corresponding block in all the frames of the second image group, and generate the integrated result of analysis of the second image group based on a sum of the weighted lesion presence probabilities.

6. The CAD apparatus of claim 4, wherein the at least one processor is further configured to:
   re-determine a lesion area in each frame of the second image group by performing backtracking in reverse of an order of receiving all frames of the sequence group based on the integrated result of analysis of the sequence group and the integrated result of analysis of the second image group.

7. The CAD apparatus of claim 1, wherein the at least one processor is further configured to:
   perform preprocessing on the received consecutive medical images, the preprocessing comprising one or more of normalization, channel separation, and scaling.

8. A computer-aided diagnosis (CAD) method comprising:
   receiving, at at least one processor, consecutive medical images;
   generating at least one sequence group by grouping, at the at least one processor, the received consecutive medical images by a predetermined number of consecutive images;
   separating, at the at least one processor, images included in each sequence group into a first image group and a second image group, wherein the first image group comprises at least one reference image comprising a first frame in the each sequence group, and the second image group comprises other frames included in the each sequence group;
   analyzing, at the at least one processor, the first image group using a first analytical algorithm, and analyzing the second image group using a second analytical algorithm that is different from the first analytical algorithm in parallel; and
   outputting, on a screen, a result of the analyzing of the first image group and the second image group,
   wherein the separating comprises separating the first image group and the second image group based on at least one a performance of the CAD, a processing rate of the first analytical algorithm, and a processing rate of the second analytical algorithm,
   wherein the analyzing of the second image group comprises analyzing all frames of the second image group in sequence using the second analytic algorithm by measuring a variation in each block, among blocks of the frames of the of the second image group, between a specific frame and a previous frame thereof in the second image group, and analyzing the specific frame based on the measured variation, and
   wherein the analyzing of the second image group comprises calculating a lesion presence probability for each block in all the frames of the second image group based on the measured variation, and detecting a lesion area in each of the frames of the second image group based on the calculated lesion presence probability.

9. The CAD method of claim 8, wherein the second analytical algorithm requires less analysis time in comparison to the first analytical algorithm.

10. The CAD method of claim 8, wherein the analyzing of the first image group comprises analyzing an entire area of the at least one reference image on a pixel-by-pixel basis or on a predetermined pixel group-by-pixel group basis using the first analytical algorithm.

11. The CAD method of claim 8, wherein the analyzing of the first image group and the second image group comprises:
   generating an integrated result of analysis of the second image group by combining results of analysis of all frames of the second image group; and
   generating an integrated result of analysis of the sequence group by combining a result of analysis of the first image group and the integrated result of analysis of the second image group.

12. The CAD method of claim 11, wherein the generating of the integrated result of analysis of the second image group comprises assigning a preset weighted value to a lesion presence probability for each block in each of all the frames of the second image group, adding weighted lesion presence probabilities for a corresponding block in all the frames of the second image group, and generating the integrated result of analysis of the second image group based on a sum of the weighted lesion presence probabilities.

13. The CAD method of claim 11, wherein the analyzing of the first image group and the second image group further comprises re-determining a lesion area in each frame of the second image group by performing backtracking in reverse of an order of receiving all frames of the sequence group based on the integrated result of analysis of the sequence group and the integrated result of analysis of the second image group.

14. The CAD method of claim 8, further comprising:
   performing preprocessing on the received consecutive images, the preprocessing which comprises one or more of normalization, channel separation, and scaling.

* * * * *